US009585741B2

(12) United States Patent
Ma

(10) Patent No.: US 9,585,741 B2
(45) Date of Patent: Mar. 7, 2017

(54) EMBOLUS REMOVAL DEVICE WITH BLOOD FLOW RESTRICTION AND RELATED METHODS

(71) Applicant: Jianlu Ma, Irvine, CA (US)

(72) Inventor: Jianlu Ma, Irvine, CA (US)

(73) Assignee: NeuroVasc Technologies, Inc, Laguna Hills, CA (US)

( * ) Notice: Subject to any disclaimer, the term of this patent is extended or adjusted under 35 U.S.C. 154(b) by 0 days.

(21) Appl. No.: 14/598,705

(22) Filed: Jan. 16, 2015

(65) Prior Publication Data

US 2015/0150672 A1 Jun. 4, 2015

Related U.S. Application Data

(63) Continuation-in-part of application No. 14/082,019, filed on Nov. 15, 2013.

(Continued)

(51) Int. Cl.
*A61M 29/00* (2006.01)
*A61F 2/01* (2006.01)
(Continued)

(52) U.S. Cl.
CPC .......... *A61F 2/013* (2013.01); *A61B 17/1204* (2013.01); *A61B 17/12031* (2013.01);
(Continued)

(58) Field of Classification Search
CPC ........ A61B 17/12022; A61B 17/22032; A61B 17/221; A61B 2017/00557;
(Continued)

(56) References Cited

U.S. PATENT DOCUMENTS 7,232,452 B2 * 6/2007 Adams ............. A61B 17/12136
606/200
2009/0069828 A1 * 3/2009 Martin ................. A61B 17/221
606/159

(Continued)

FOREIGN PATENT DOCUMENTS

EP          1 867 290 A1    12/2007
WO    WO2012/009675 A2     1/2012
(Continued)

OTHER PUBLICATIONS

Supplementary European Search Report dated Aug. 8, 2016 in corresponding European application No. EP 14 75 3862.

*Primary Examiner* — Jonathan Miles
*Assistant Examiner* — Kankindi Rwego
(74) *Attorney, Agent, or Firm* — Raymond Sun

(57) ABSTRACT

The present invention provides devices for removing an embolus or thrombus. The device includes an elongate member configured for insertion into the vasculature, an expandable member that extends from the distal end of the elongate member, and a flow restrictor associated with a proximal portion of the expandable member. The expandable member is configured to transition from a compacted state to an expanded state, in which the expandable portion engages with the embolus. The flow restrictor is configured to restrict blood flow and generate a low pressure zone at a location in the vasculature that is distal to the flow restrictor.

12 Claims, 11 Drawing Sheets

Related U.S. Application Data

(60) Provisional application No. 61/832,786, filed on Jun. 8, 2013, provisional application No. 61/768,336, filed on Feb. 22, 2013.

(51) Int. Cl.
*A61B 17/221* (2006.01)
*A61B 17/12* (2006.01)
*A61B 17/29* (2006.01)

(52) U.S. Cl.
CPC .. *A61B 17/12036* (2013.01); *A61B 17/12177* (2013.01); *A61B 17/221* (2013.01); *A61B 2017/1205* (2013.01); *A61B 2017/2212* (2013.01); *A61B 2017/2215* (2013.01); *A61B 2017/2905* (2013.01); *A61F 2002/015* (2013.01); *A61F 2002/016* (2013.01); *A61F 2002/018* (2013.01); *A61F 2230/0067* (2013.01); *A61F 2230/0071* (2013.01)

(58) Field of Classification Search
CPC .. A61B 2017/2215; A61B 2017/22051; A61B 17/12109; A61B 17/1214; A61B 17/12168; A61B 17/12172; A61B 17/12177; A61B 17/22; A61B 17/22031; A61B 17/22034; A61B 17/22035; A61B 2017/22048; A61B 2017/22049; A61B 2017/22052; A61B 2017/22054; A61B 2017/22055; A61F 2/01; A61F 2/02; A61F 2/013; A61F 2/82; A61F 2/04; A61F 2/042; A61F 2/86; A61F 2/88; A61F 2/885; A61F 2/89; A61F 2/90; A61F 2002/011; A61F 2002/015; A61F 2002/016; A61F 2002/018; A61F 2002/821; A61F 2002/823; A61F 2002/825; A61F 2002/828; A61F 2/06; A61F 2/064; A61F 2002/041; A61F 2002/043; A61F 2002/044; A61F 2002/046; A61F 2002/047; A61F 2002/048; A61F 2002/061; A61F 2002/062; A61F 2002/065; A61F 2002/067; A61F 2002/068
USPC ....... 606/108, 127, 159, 191, 192, 194, 200; 604/19, 48, 96.01, 97.01
See application file for complete search history.

(56) References Cited

U.S. PATENT DOCUMENTS

| | | | |
|---|---|---|---|
| 2011/0009941 A1* | 1/2011 | Grandfield | A61F 2/91 623/1.11 |
| 2011/0130784 A1 | 6/2011 | Kusleika | |
| 2011/0251629 A1 | 10/2011 | Galdonik et al. | |
| 2011/0264132 A1 | 10/2011 | Strauss et al. | |
| 2011/0282461 A1* | 11/2011 | Shin | A61F 2/90 623/23.7 |
| 2012/0083868 A1 | 4/2012 | Shrivastava et al. | |

FOREIGN PATENT DOCUMENTS

| | | |
|---|---|---|
| WO | WO2013/025531 A1 | 2/2013 |
| WO | WO2015/057796 | 4/2015 |

* cited by examiner

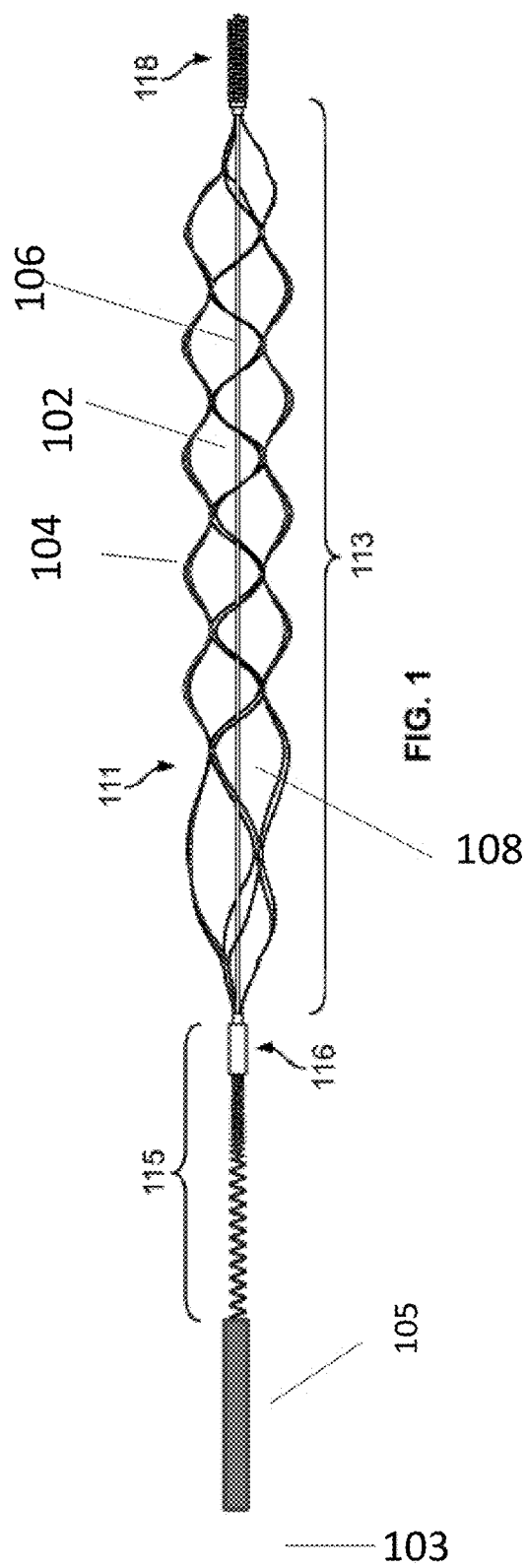
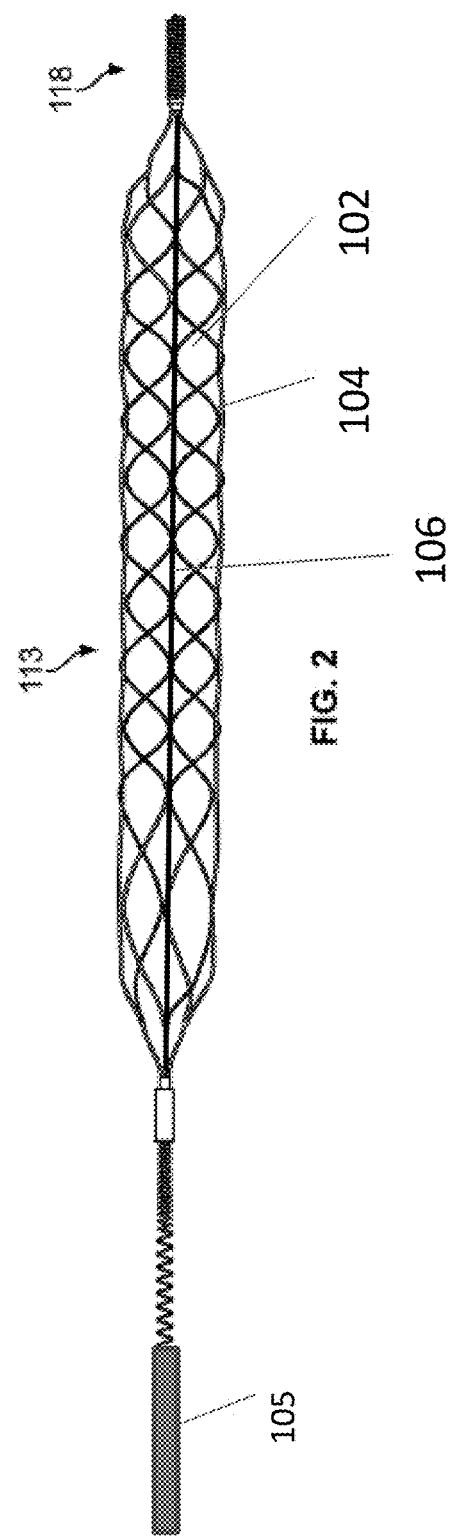

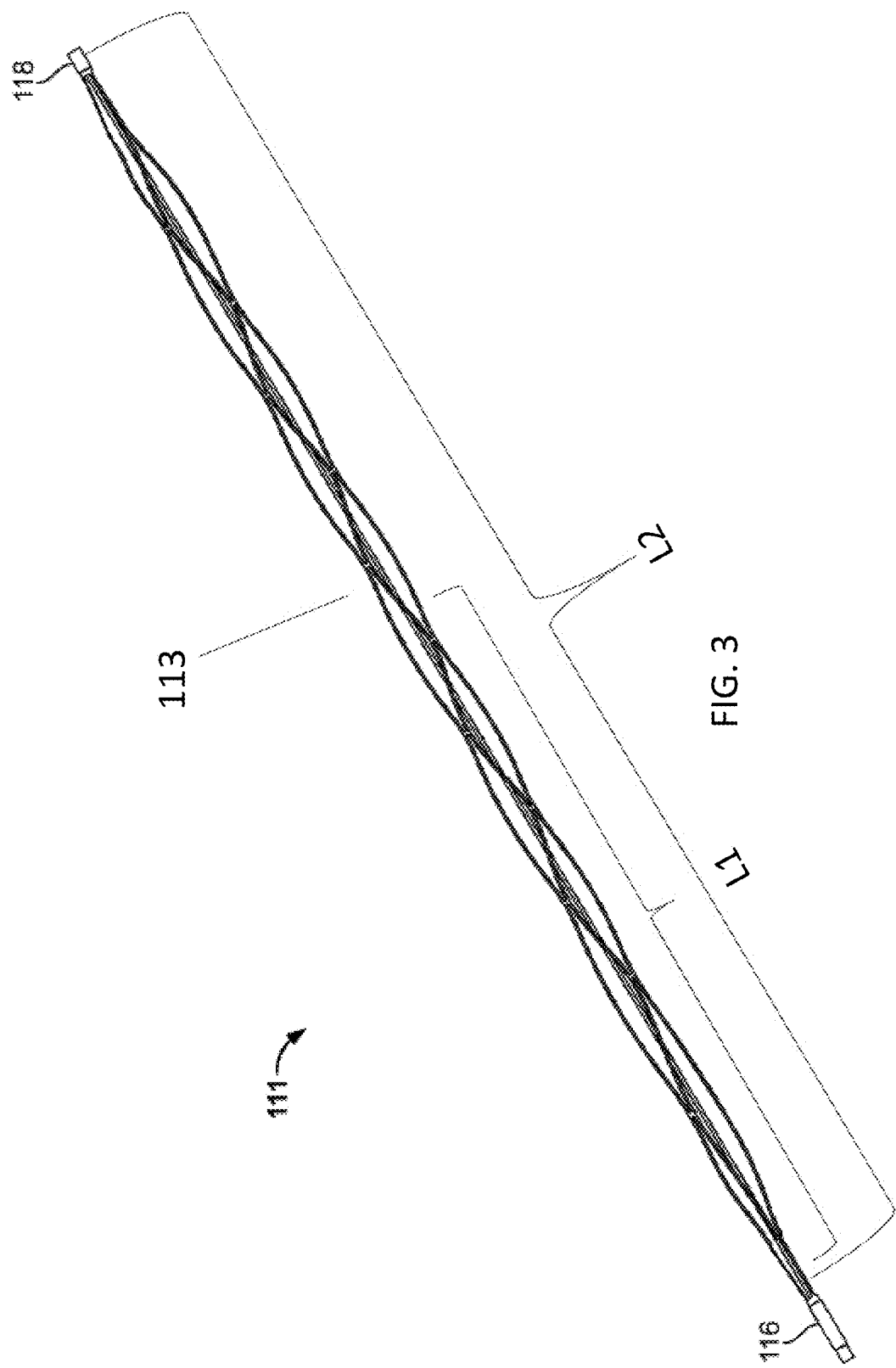

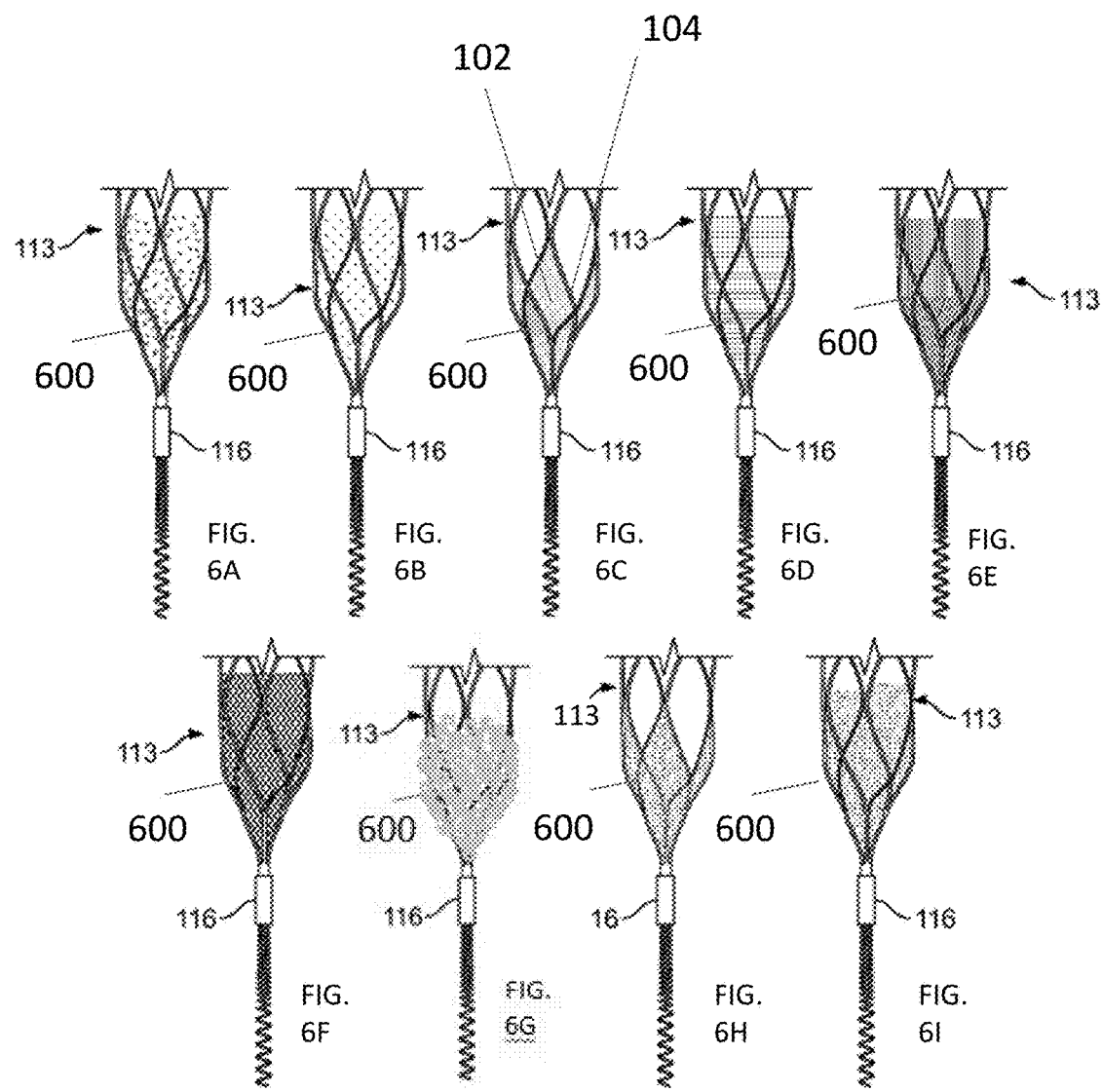

EMBOLUS REMOVAL DEVICE WITH BLOOD FLOW RESTRICTION AND RELATED METHODS

CROSS-REFERENCE TO RELATED APPLICATIONS

This application is a continuation-in-part of U.S. Nonprovisional Ser. No. 14/082,019, filed Nov. 15, 2013, which claims the benefit of and priority to U.S. Provisional Ser. No. 61/768,336, filed Feb. 22, 2013, and U.S. Provisional Ser. No. 61/832,786, filed Jun. 8, 2013. The contents of the aforementioned applications are incorporated by this reference as if fully set forth herein in their entirety.

TECHNICAL FIELD

This invention generally relates to devices and methods useful for clot retrieval and removal devices to treat, among other things, ischemic stroke.

BACKGROUND

Currently, the FDA-approved treatment options for an acute ischemic stroke include intravenous (IV) delivery of clot dissolving medicine and mechanical thrombectomy.

For treatment use clot dissolving medicine, the thrombolytic agent (Tissue Plasminogen Activator (t-PA)) is injected into the vasculature to dissolve blood clots that are blocking blood flow to the neurovasculature. Intravenous t-PA is currently limited in use because it must be used within a three hour window from the onset of a stroke and can result in an increased risk of bleeding. This standard of care leaves room for upgrading, lower aisle profiles and is only the appropriate approach to treatment for a limited class of individuals, groups and temporally-limited exigent cases.

The second option includes using mechanical thrombectomy devices. Such devices are designed to physically capture an embolus or clot and remove it from the blocked vessel, thereby restoring blood flow. The major advantage of the mechanical thrombectomy device is it can expand the treatment windows from 3 hours to over 10 hours.

Some existing mechanical thrombectomy devices used for increasing blood flow through an obstructed blood vessel include: 1) a filter trap designed and built to collect and remove emboli; 2) a cork-screwed guidewire like device to retrieve embolus; and 3) a stent like device connected to a delivery wire to retrieve embolus. Filter thrombectomy devices suffer from the following disadvantages. The filters tend to be cumbersome and difficult to delivery, deploy and a larger profile guide catheter may be needed to fully remove the embolus. In addition, it is difficult to coordinate precisely and predictably a desired movement to position the device properly in the vessel. The device can drift within the vessel, twist, or not be adequately conforming to the vessel wall and, therefore not effective for removing embolus. Corkscrewed guidewire devices pose a disadvantage because they can only capture and remove emboli that are firm or subject to certain mechanical variables such as being held together by itself as one piece. Stent-like mechanical thrombectomy devices are not capable of capturing small emboli that break off from the large embolus if any, and can lead to complications such as blockage of distal smaller vessels, vessel dissection, perforation and hemorrhage arise as a result of over-manipulation in the vessel.

Disadvantages common to all of the devices described above include, for example: 1) the device may capture an embolus, but then lose grasp of it and migrate/deposit it incidentally in another area of the neurovasculature, creating the potential for a new stroke in a different part of the neurovasculature; 2) the device is not capable to capture the small embolus break off from the major embolus and prevent it from migrating to a more distal area of the neurovasculature; 3) the relative large device profile prevents it from treating the distal small diameter vessels.

Another disadvantage to existing mechanical thrombectomy devices is that they are built using two or more distinct pieces that require either joints or bonding between the delivery system and the treatment device. This connection of the pieces generally results in a weakness in the device that can result in an unintentional separation of the two pieces, possibly leaving the treatment device in the body during embolus retrieval. Also, the treatment portion of mechanical thrombectomy devices (particularly stent like devices) tend to be cut from tubing that is larger than the delivery system, thus making the treatment portion the limiting factor in terms of minimizing the compacted profile of the device, requiring larger access systems and greater delivery force to deliver the device.

Other flaws in the current mechanical thrombectomy designs include poor visibility/radiopacity, lack of variation in the delivery portion to enhance and improve deliverability, and lack of coatings or modified surface textures on the treatment portion to enhance embolus affinity, etc. In conclusion, there is a great need for improved devices, device systems, and methods for increasing blood flow through a blood vessel as described herein. None of the existing medical mechanical thrombectomy devices address all necessary needs to date.

SUMMARY OF THE DISCLOSURES

The present invention is directed to a device for removing emboli and other luminal blockages. Devices of the invention include, generally, an expandable treatment member for removing an embolus and a flow restrictor associated with a proximal end of the expandable treatment member. The expandable treatment member is typically an expandable cage or mesh coupled to an elongate delivery shaft. In use, the expandable member is position within or distal to an embolus within a blood vessel and then transitioned into an expanded state. Expansion of the expandable treatment member engages the treatment member with the blockage (e.g., thrombus, embolus, atheroma, fatty deposits, etc.). In addition, the expansion of the treatment member causes the proximal flow restrictor to likewise expand. During treatment, expansion of the proximal flow restrictor advantageously limits or restricts forward blood flow and creates a low pressure zone within the blood vessel at locations distal to the flow restrictor. The low pressure zone acts like a vacuum to assist in removal of the embolus from the blood vessel. After expansion, the expandable treatment member and the emboli engaged with the treatment member are removed from the blood vessel.

According to certain aspects, devices of the invention include an elongate member comprising a distal end, an expandable treatment member extending from the distal end of the elongate member, and a flow restrictor associated with a proximal portion of the treatment member. The elongate member is configured to deliver the expandable treatment member to a treatment site within a body lumen (e.g., location of embolus within a blood vessel). The expandable treatment member transitions from a compacted state to an expanded state. During delivery, the expandable treatment member is preferably in the compacted state to allow for easy transport of the expandable treatment member to the location of the embolus. The expandable treatment member may be expanded within or distal to the embolus to engage the embolus for removal. The expandable treatment member can also be expanded in a location in the vessel, so that the embolus is located in a position between the proximal restrictor and the distal end of the expandable treatment member; in other words, at least portion of the expandable treatment member is distal to the embolus. The flow restrictor is associated with a proximal portion of the expandable treatment member, and expands in conjunction with the expansion of the expandable treatment member. The proximal flow restrictor functions generally as described above.

The components (delivery member 105, expandable member 113, or transition member 115) of the removal device 111 may be formed from separate pieces of material or formed from a single piece of material. In certain embodiments, the elongate delivery member and the expandable treatment member are constructed from a single/unitary piece of material, thus eliminating any joints or bonding of the separate members together. This construction improves the strength of the system as a whole and greatly reduces the possibility of the two members unintentionally detaching from each other during extraction of the embolus. In addition, the elongate delivery member and the treatment member, when compacted, may have the similar size profile which reduces the amount of force required for delivery and provides access into smaller vessels or other lumens.

In certain embodiments, the expandable treatment member is a frame with plurality of openings. Frame members or struts form the body of the frame and define the plurality of openings. In certain embodiments, the frame members are a plurality of intersecting wires or other threads. The frame members may form a mesh or cage-like structure that defines a plurality of openings. When expanded, the frame receives the embolus through the openings and within the frame, thereby engaging the embolus for removal. In certain embodiments, the expandable treatment member comprises a plurality of protrusions on the frame. The plurality of protrusions further engages the embolus for removal. As an alternative to or in addition to the plurality of protrusions, the expandable treatment member may include one or more surface modifications or treatments. For example, the surface of the expandable treatment member may be rough to improve clot adhesion.

As discussed, the flow restrictor restricts forward blood flow and generates low pressure within a vessel at locations distal to the flow resistor in order to assist in removal of the embolus or other blockage. Preferably, the flow restrictor is designed to transition from a compacted state to an expanded state in response to the expansion of the expandable treatment member. In certain embodiments, the flow restrictor surrounds an inner surface or diameter of a proximal portion of the expandable treatment member. In other embodiments, the flow restrictor surrounds an outer surface or diameter of a proximal portion of the expandable treatment member. In further embodiments, the flow restrictor surrounds both the inner and outer surfaces or diameters of the proximal portion of the expandable treatment member. The flow restrictor may cover a length extending between a proximal end of the expandable member to about ½ of the length of the expandable member. In other embodiments, the flow restrictor may cover a length extending between a proximal end of the expandable member to about ¼ of the length of the expandable member. The flow restrictor is typically a film, membrane, or netted material. In certain embodiments, the flow restrictor is a polymeric film or membrane. In other embodiments, the flow restrictor is a braided or woven net formed from a metal, polymer, or combination thereof. The type and material of the flow restrictor may be chosen based on the desired coverage (i.e. amount of flow to be restricted).

A medical mechanical thrombectomy device and methods useful for increasing blood flow through a blood vessel are described herein. In general, a device system includes an elongate member (proximal portion) and an expandable member (distal portion) fabricated from a single piece of super elastic or shape memory biocompatible material (tubing). The expandable member is configured to be inserted into a blood vessel and defines multiple spaces/openings in a wall of the expandable member. The expandable member generally has a compacted configuration for delivery and insertion into the target location of a blood vessel and an expanded configuration in which the expandable member to engage/receive embolus/clots with the multiple space/openings on it. The proximal portion/end of the expandable member has a flow block feature to block the blood flow when the device is expanded during the procedure.

The device can be made from either metallic biocompatible material (such as Nitinol, stainless steel, Co—Cr base alloy, Ta, Ti, etc.) or polymer based biocompatible material (polymers with shape memory effect, PTFE, HDPE, LDPE, Dacron, Polyester, etc.). For ischemic stroke treatment, the expandable stent-like member must be flexible enough to negotiate the torturous vasculature of the brain and without modifying the vessel profile at the target location. The profile of the expandable stent-like member must be small enough to reach target treatment site as known to artisans.

The expandable member can be fully or partially coated with chemical(s), drug(s) or other bioagents to prevent clotting and/or for the better adhesion between the device and embolus. The device surface can be treated to form different surface layer (oxidation layer, Nitro or carbonized or N—C-combined surface layer, etc.) for better adhesion between device and embolus. The device strut surface can be mechanically, chemically, or electrochemically treated to form "rough" surfaces for better adhesion between devices and emboli.

Radiopaque markers (marker coils, marker bands, Radiopaque wire(s), Radiopaque coatings, etc.) are integrated into the treatment device on the distal portion and proximal portion; or through the entire inner lumen of the treatment portion either partially or entirely to help visualize and position the device under standard fluoroscopy equipment.

The transition portion of the device is between the delivery portion and expandable treatment member. In embodiments that include a delivery portion and expandable member are formed from a unitary piece of material, the transition portion is seamless because no joints or bonding are required to connect the delivery portion to the expandable treatment member. The transition portion may be modified with a number of variations to vary flexibility by having straight tubing, spiral cut through the wall thickness, or spiral cut partially through the wall thickness. When spiral cut, the flexibility can be varied through variable pitch sizes across the length. The transition portion can be covered by polymer tubing/layers/covers for the optimization of the device deliverability and the surface smoothness.

The inner lumen in the entire device can be used for the local drug delivery in the vasculature if needed. Following paragraphs describe the details of each device component.

BRIEF DESCRIPTION OF THE DRAWINGS

For a more complete understanding of the invention, reference is hereby made to the drawings, in which:

FIG. 1 depicts a side profile of the clot removal device, according to embodiments of the present disclosure;

FIG. 2 depicts a side profile of the clot removal device of FIG. 1 from another angle.

FIG. 3 depicts the expandable treatment member in the extended position.

FIG. 6A-6I are illustrate proximal flow restrictors on the proximal portions of the expandable member.

DETAILED DESCRIPTION

Figure 4A:
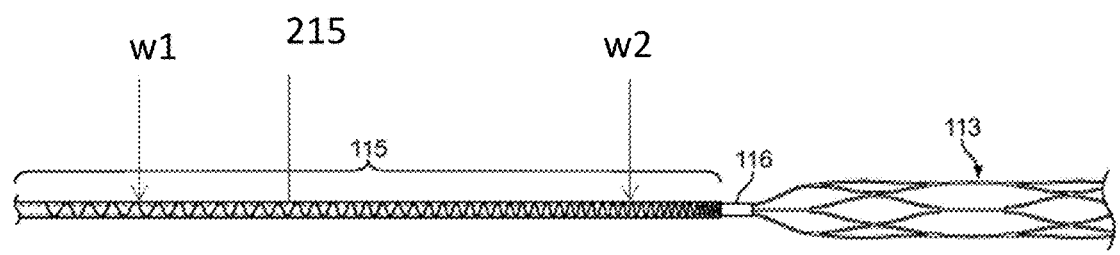
FIG. 4A is an example of a transition portion of the device with a spiral cut through the entire wall thickness.

The present invention is directed to a device for removing emboli and other luminal blockages. The device includes an expandable treatment member, such as mesh or cage, that is associated with a proximal flow restrictor. During treatment, the expandable treatment member is position within or distal to an embolus within a blood vessel and then transitioned into an expanded state. In certain embodiments, the expandable treatment member's normal state is the expanded configuration, and the expandable treatment member is compacted and delivered to the treatment site in the compacted configuration through a delivery sheath. The expandable treatment member is deployed from the delivery sheath, which causes it to return to its normal expanded profiled by the elastic energy stored in the device. Expansion of the expandable treatment member engages the expandable treatment member with the blockage (e.g., thrombus, embolus, atheroma, other fatty deposits, etc.). In addition, the expansion of the expandable treatment member causes the proximal flow restrictor to likewise expand. Expansion of the proximal flow restrictor advantageously limits or restricts forward blood flow and creates a low pressure zone within the blood vessel at locations distal to the flow restrictor. The low pressure zone acts like a vacuum to assist in removal of the embolus from the blood vessel. After expansion, the expandable treatment member and the emboli engaged with the expandable treatment member are removed from the blood vessel.

In certain embodiments, the expandable treatment member's normal state is the expanded configuration, and the expandable treatment member is compacted and delivered to the treatment site in the compacted configuration through a delivery sheath. The expandable treatment member is deployed from the delivery sheath, which causes it to return to its normal expanded profiled by the elastic energy stored in the device.

Devices of the invention are suitable for removal of blockages in body lumens, and are particularly well suited for removal of thrombi, emboli, or atheroma in the vasculature, including those in arteries and veins. It is understood that the dimensions of the device may be modified to suit a particular application. For example, devices of the invention used for treatment of deep vein thrombosis may have a larger cross-section than devices of the invention used for treatment of brain ischemia.

The delivery devices of the invention are described in more detail below with reference to the figures.

FIGS. 1 and 2 illustrate various views of the clot removal device according to certain aspects. FIG. 1 illustrates a front view of the clot removal device, and FIG. 2 illustrates a side view of the clot removal device of FIG. 1. As indicated in FIGS. 1 and 2, the clot removal device 111 includes a proximal end 103 and a distal end 101. The clot removal device 111 includes the following main components: a delivery member 105, a transition member 115, and expandable treatment member 113. Note: the components of FIGS. 1 and 2 are not drawn to scale in relationship to each other.

The delivery member 105 is an elongate body or shaft. The delivery member 105 terminates at the proximal end 103 of the device 111. The delivery member 105 is designed to push or drive the expandable member to a treatment site (e.g. location at or near the embolus). Preferably, the delivery portion is formed from a material of enough rigidity to drive the expandable member through the vasculature. In certain embodiments, the proximal end of the delivery member 105 includes a handle for easy maneuvering of the device 111 within the vasculature. The delivery member 105 may about 40 cm or longer. In some embodiments, the delivery member 105 is about 100 cm or longer. In some embodiments, the delivery member 105 is about 190 cm or longer. A distal end of the delivery member 105 is associated with the proximal end of the transition member 115. In some embodiments, the delivery member 105 is coupled to the transition member 115, e.g. via a joint. In other embodiments, the delivery member 105 is formed from the same unitary piece of material as the transition member 115 such that the delivery member 105 seamlessly changes into the transition member 115.

The transition member 115 is typically more flexible than the delivery member 105. The flexibility of the transition portion 115 allows the delivery of the expandable member 113 through the tortuous vasculature. The transition member 115 may be of the same flexibility or rigidity across its length or the transition member 115 may have variable flexibility or rigidity across its length. For example, a proximal end of the transition member 115 may be more rigid than the distal end of the transition member 115. The length of the transition member 115 may depend on the treatment application of the device 111. For example, the transition member 115 may be smaller in devices used to remove cerebral emboli and may be larger in devices used to remove emboli near the heart or deep vein. Suitable lengths for the transition member 115 range, for example, from about 5 cm to about 50 cm. A distal end of the transition member 115 is associated with a proximal end of the expandable treatment member 113. In some embodiments, the transition member 115 is coupled to the expandable treatment member 113, e.g. via a joint. In other embodiments, the transition member 115 is formed from the same unitary piece of material as the expandable treatment member 113 such that the transition member 115 seamlessly changes into the expandable treatment member 113.

Figures 11A, 11B:
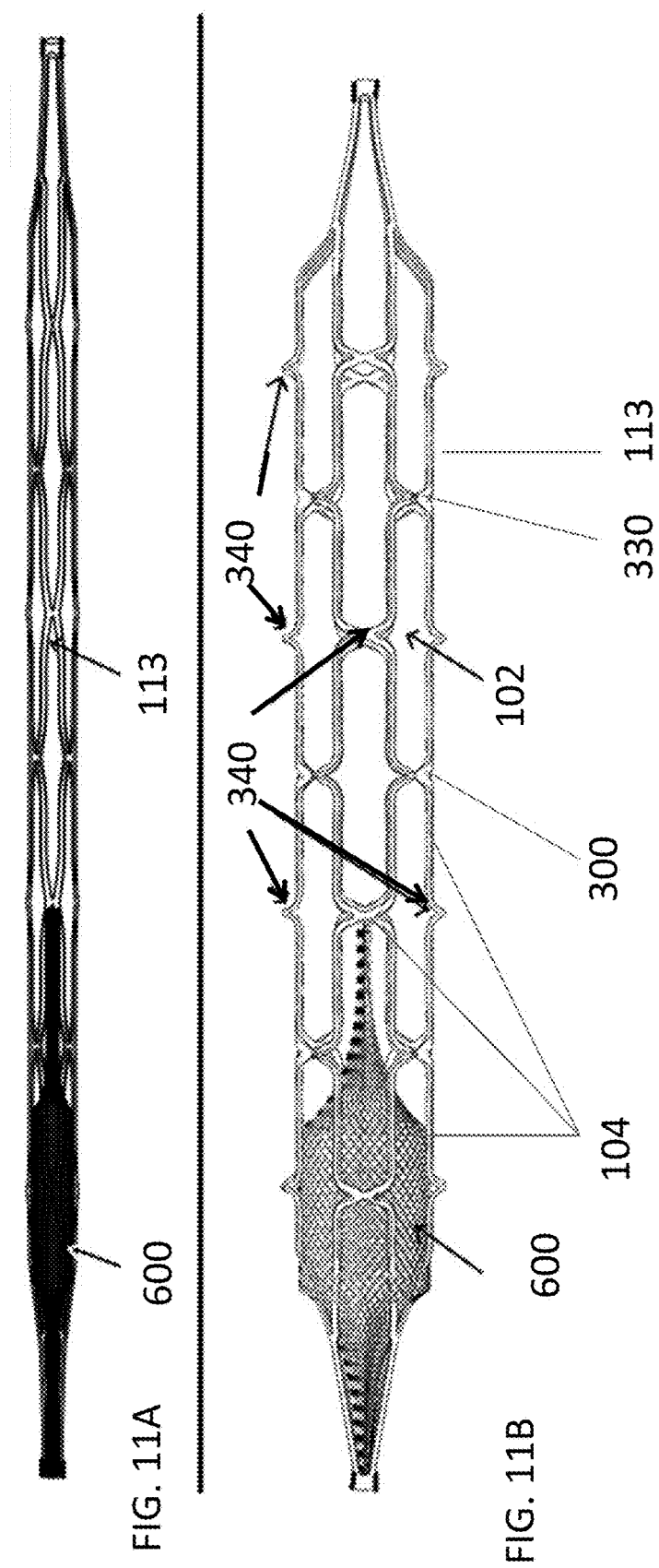
FIG. 11A illustrates the expandable treatment member and flow restrictor in the compacted configuration, according to certain embodiments. The flow restrictor is inside the inner surface/diameter of the expandable treatment member.
FIG. 11B illustrates the expandable treatment member and flow restrictor in the expanded configuration, according to certain embodiments. The flow restrictor is inside the inner surface/diameter of the expandable treatment member.
Figure 12A:
FIG. 12A illustrates a cross-section of the expandable treatment member in the compacted configuration, according to certain embodiments.
Figure 12B:
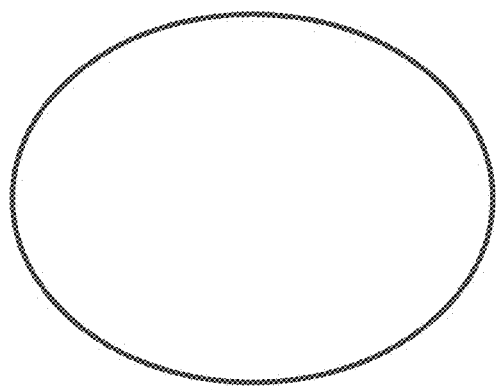
FIG. 12B illustrates a cross-section of the expandable treatment member in the extended configuration, according to certain embodiments.

The expandable treatment member 113 is used to remove the embolus or other blockage within a vessel. The expandable treatment member 113 transitions from a compacted configuration to an expanded configuration. When in the compacted configuration, the expandable treatment member 113 has a smaller cross-section than when the expandable treatment member 113 is in the expanded configuration. In certain embodiments, the body or frame of the expandable treatment member 113, when in the compacted configuration, is elongated. FIG. 11A illustrates the expandable treatment member 113 in the elongated, compacted configuration, and FIG. 11B illustrates the expandable treatment member 113 in a shorter, expanded configuration. In other embodiments, the body or frame of the expandable treatment member 113, when in the compacted configuration, is condensed, folded, or wrapped around itself. FIG. 12A illustrates an exemplary cross-section of the expandable treatment member 113 wrapped and folded around itself, while in the compacted configuration. FIG. 12B illustrates the same cross-section of the expandable treatment member 113 when in the unwrapped, expanded configuration.

Typically, the expandable treatment member 113 transitions from the compacted configuration to the expanded configuration when the expandable treatment 113 is deployed/released from an outer delivery sheath, like microcatheter, used in conjunction with and surrounding the removal device 111. In use, the expandable member 113 is either positioned within the embolus or distal to the embolus and then deployed. The expandable treatment member 113 can also have a length longer than that of the embolus, in use, the expandable treatment member 113 can go beyond both ends of the embolus (for example, embolus locate in the middle portion of the expandable treatment portion), and to engage embolus to remove it from the vessel. Upon deployment, the expandable treatment member 113 expands to engage with the embolus for removal. In dealing with long emboli, the device can also be used to remove the embolus from the proximal portion to distal with multiple passes, until entire embolus is removed.

According to certain embodiments, the body or frame of the expandable treatment member 113 includes frame members 104 (or struts) that define a plurality of openings 102. The frame members 104 also define an inner lumen 108. In certain embodiments, the frame members 104 are a plurality of intersecting wires or threads. The configuration of the frame members 104 may form a mesh or cage-like support structure. The frame members 104 of the expandable member 113 may forms angles with the longitudinal axis of the device 111 in the range from at least about 5 to approximately 175 degrees. The frame members 104 can have twists along their longitudinal axes. When expanded, the expandable treatment member 113 receives the embolus within the frame, thereby engaging the embolus for removal. That is, a portion of the embolus may enter the inner lumen 108 of the expandable member 113, and thus integrating the embolus with the expandable member 113 for removal. The length of the expandable member 113 may depend on the treatment application of the device 111. Preferably, expandable member may range from about 0.5 cm to about 15 cm in length (while smaller and longer lengths are also contemplated). The expandable treatment member 113 can include a tapered distal section. The tapered distal section assists in collecting small embolus break offs from major clot(s) and preventing them from migrating to a more distal area of the vasculature.

The device 111 may also include markers 116, 118 at or near the proximal and/or distal ends of the expandable member 113. The markers 116, 118 are preferably formed from a material that is visible to an imaging modality (such as x-ray, angiogram, or other external imaging modality). In certain instances, the material is radiopaque. The markers 116, 118 may be rings, bands, wires, or coils or other elements surrounding the junctions at the proximal and distal ends of the expandable member 113. In certain embodiments, the marker 116 forms the joint between the transition member 115 and expandable member 113.

In certain embodiments, the expandable treatment member 113 includes an inner radiopaque shaft 116. The shaft 116, like markers 116, 118, increases the visibility of the expandable member 113 by external imaging modalities during the procedure. The shaft 116 may be formed as a unit with the markers 116, 118 (e.g., forming a dumbbell like structure).

In preferred embodiments, the delivery member 105, transition member 115, and expandable member 113 are all formed from a unitary piece of material. By using a unitary material to form those components, the device 111 does not include joints connecting the components. The unitary piece of material is typically tubing that is cut to form the distinct components. The device 111 is made by laser cutting, mechanical machining, chemical machining, electrochemical machining, EDM, and related techniques known to artisans. Preferably, the material is biocompatible, super elastic, and/or exhibits shape memory properties. Suitable materials include Nitinol and alloys thereof. The construction of the device 111 from a unitary piece of material dramatically reduces the possibility of an unintentional separation of the expandable member 113 from the delivery member 105 or the transition member 115.

The following describes the various components of the removal device 111 and additional features of the removal device 111.

Figure 4B:
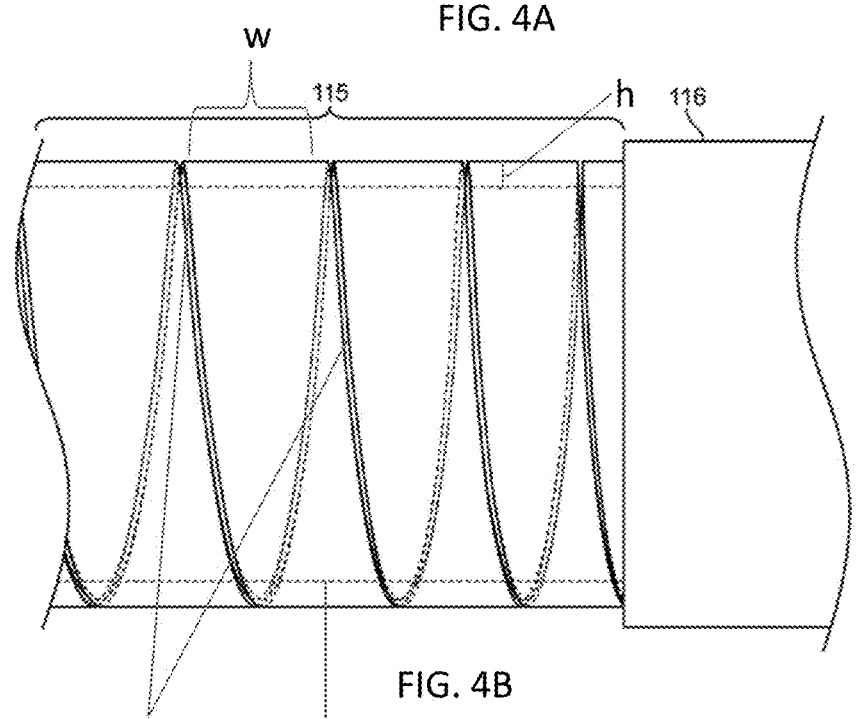
FIG. 4B is an example of a transition portion of the device with a spiral cut partially through the entire wall thickness.

FIGS. 4A-4B show examples of the transition member 115 of the design. The transition member, as shown in FIGS. 4A-4B, is a tube with a spiral cut extending partially through the thickness h of the tube. By only partially cutting into the thickness h of the tube, a plurality of grooves 216 is formed on the surface of the tube (as best shown in FIG. 4B). The width or pitch w (see FIG. 4B) of the spiral cut may be the same or vary across the length of the transition member 115. As shown in FIG. 4A, the spiral cut transitions from a first width w1 to a second width w2. Particularly, the width decreases from w1 to w2 across the length of the transition member 115.

Figure 5A:
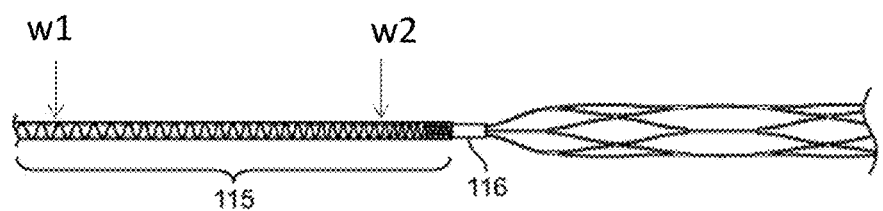
FIG. 5A is an example of a transition portion of the device with a spiral cut configuration showing variable pitch sizes.
Figure 5B:
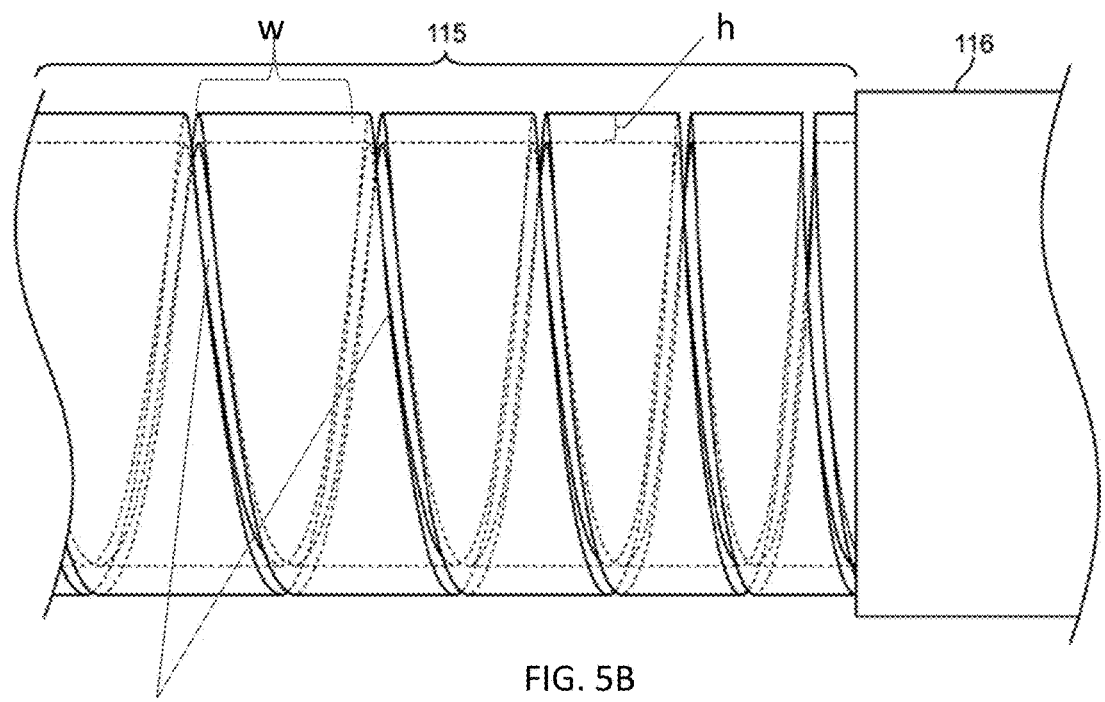
FIG. 5B is an example of a transition portion of the device with a spiral cut configuration through the entire wall thickness.

FIGS. 5A-5B show examples of the transition member 115 of the removal device 111, according to another embodiment. The transition member, as shown in FIGS. 5A-5B, is a tube with a spiral cut extending completely through the thickness h of the tube. By cutting into the entire thickness h of the tube (best shown in FIG. 5B), the tube has a spring-like profile. The width or pitch w (see FIG. 5B) of the spiral cut may be the same or vary across the length of the transition member 115. As shown in FIG. 5A, the spiral cut transitions from a first width w1 to a second width w2. Particularly, the width decreases from w1 to w2 across the length of the transition member 115.

Preferably, the device 111 of the invention includes a proximal flow restrictor. The proximal flow restrictor is associated with the proximal portion or end of the expandable treatment member 113. The proximal flow restrictor may be positioned proximal to the proximal end of the expandable member, on, within or surrounding the proximal portion of the expandable member, or both. Ideally, the proximal flow restrictor extends any length between the proximal end and the middle of the treatment member 113. The proximal flow restrictor is typically a material that at least partially surrounds the inner or outer surfaces or diameters of the proximal end of the expandable treatment member 113. The proximal flow restrictor may also be one or more layers of the material. In some embodiments, the proximal flow restrictor surrounds both the inner and outer surfaces of the treatment member 113. The proximal flow restrictor may be a mesh, membrane, or deposited coating. In addition, the flow restrictor is formed from a braided material. The mesh or membrane may have varying porosity, depending on the preferred amount of flow blockage desired. The proximal flow restrictor may be formed from a polymer, a metal, a plastic, a fabric formed from synthetic or natural fibers, etc. Specific examples of materials for the flow restrictor include Nitinol, Pt, Ta, Co—Cr, stainless steel, polyether ether ketone, polytetrafluoroethylene, polyether block amides, polyethylene, and combinations thereof. Preferably, the flow restrictor is biocompatible.

The proximal flow restrictor may be formed as part of the expandable member 113 or coupled to the expandable member 113. One end (either proximal or distal end) of the flow restrictor can be loose or free to move, to accommodate the length change or variation during the delivery and expansion processes. The proximal flow restrictor may be coupled to the expandable member mechanically, thermally (laser or soldering), chemically, adhesively, or using heat shrink technology.

Like the expandable member 113, the proximal flow restrictor can have a first smaller compacted profile to make the delivery through a delivery sheath or microcatheter possible. The flow restrictor can have a second larger expanded diameter/profile when the device is deployed from the delivery sheath to block, limit, or restrict the blood flow. Typically, the flow restrictor expands in unison or in response to the expansion of the expandable treatment member 113, as described hereinafter. During a thrombectomy procedure using the present device 111, the proximal flow restrictor expands in response to expansion of the expandable treatment member 113. The expansion of the proximal flow restrictor advantageously limits or restricts forward blood flow and creates a low pressure zone within the blood vessel at locations distal to the flow restrictor. The low pressure zone acts like a vacuum to assist in removal of the embolus from the blood vessel.

FIGS. 6A-6I illustrate various embodiments of the proximal flow restrictor 600 on the expandable treatment member 113. FIGS. 6A and 6B illustrate the proximal flow restrictor 600 of varying porosity. The greater the porosity the lesser the vacuum created in the vessel due to the presence of the flow restrictor 600. As shown in both FIGS. 6A and 6B, the flow restrictor 600 is uniformly covering the proximal portion of the expandable member 13. FIG. 6C illustrates a flow restrictor that only covers the proximal openings 102 formed by the frame members 104 of the proximal portion of the expandable member 113. The proximal flow restrictor 600 may have various patterns or textures for restricting blood flow. FIG. 6D illustrates a flow restrictor 600 with horizontal texture, and FIG. 6E illustrates a flow restrictor 600 with vertical texture. FIG. 6F illustrates a flow restrictor 600 formed from a braided or netted material. FIGS. 6G-6I illustrates flow restrictors 600 formed from deposition processes with different coverage patterns. The deposition processes may include, for example, physical vapor deposition, chemical vapor deposition, etc. FIG. 6G illustrates a deposited flow restrictor 600 surrounding the outer surface of the expandable treatment member 113. FIG. 6H illustrates a deposited flow restrictor 600 disposed within the proximal openings 102 of the expandable treatment member 113. FIG. 6I illustrates a deposited flow restrictor 600 covering a proximal portion of the expandable treatment member 113.

Figure 8:
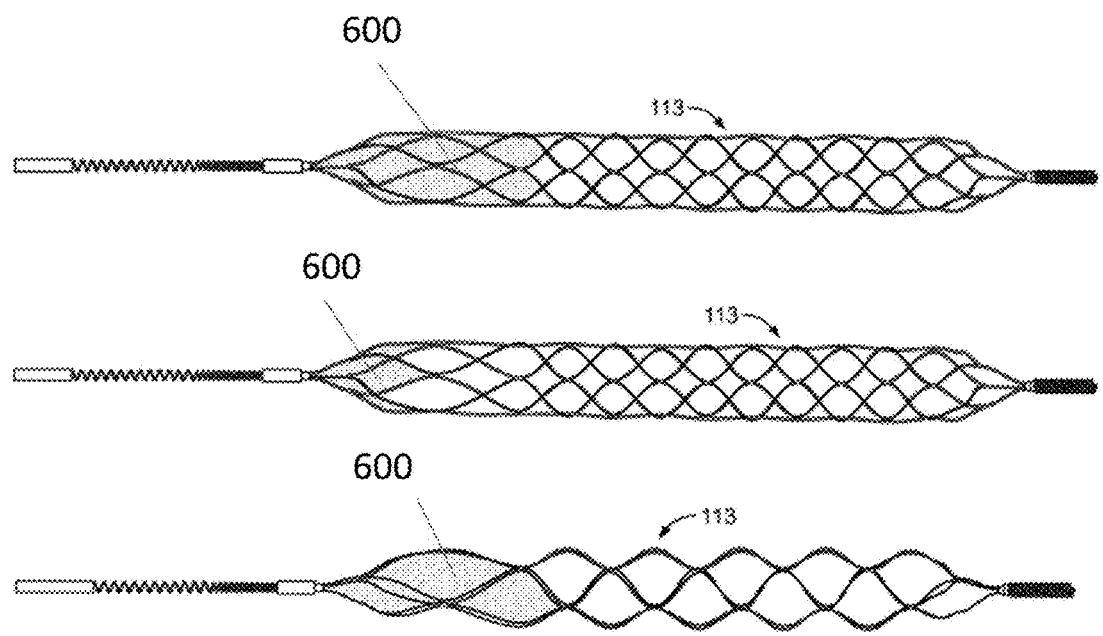
FIG. 8 illustrates front and side views of a proximal flow restrictor, according to certain embodiments.

In addition, FIG. 8 illustrates front, back, and side views of a proximal flow protector 600, according to certain embodiments.

Figure 7:
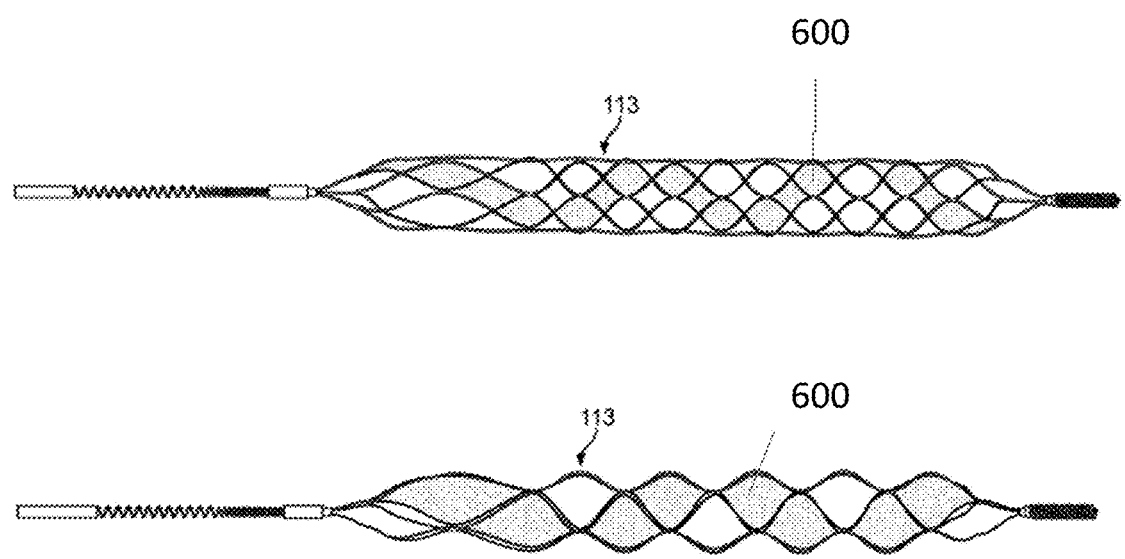
FIG. 7 illustrates a flow restrictor extending across the expandable treatment member.

The flow restrictor 600 may expand across a length of the expandable treatment member 113 from the proximal end toward the distal end. The length may be, for example, ¼, ⅓, ½, ⅔, ¾ of the body or the entire length of the body. In certain embodiments, the flow restrictor 600 may extend (partially or entirely) from the proximal end to the distal end of the expandable member 113 with varying degrees of coverage. For varying coverage, the flow restrictor may be present on the expandable member 113 in varying patterns. FIG. 7 illustrates a front view and a side view of an expandable member 113 with a proximal flow restrictor 600 having a spiral pattern across its entire length.

Figure 9:
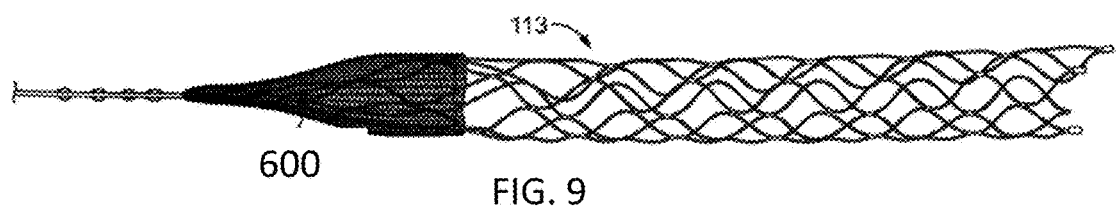
FIG. 9 illustrates a braided proximal flow restrictor surrounding the outer diameter of a proximal portion of the expandable member.

The flow restrictor 600 may also have different profiles. Typically, the flow restrictor 600 substantially conforms to an inner or outer surface of the expandable member 113. FIG. 9 illustrates proximal flow restrictor 600 that is a braided net conforming to the proximal end of expandable member 113. Alternatively, the flow restrictor 600 may have a different shape than the proximal portion of the expandable member 113. For example, the flow restrictor may have a spherical (FIG. 10), cylindrical or rectangular shape, which can be within a proximal portion of the expandable treatment member 113, proximal to the expandable treatment member (FIG. 10), or surrounding a proximal portion of the expandable treatment member.

Figure 10:
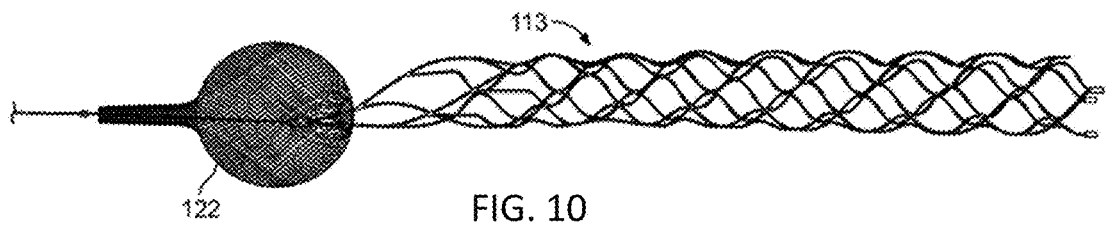
FIG. 10 illustrates a spherical proximal flow restrictor.

FIG. 10 shows an exemplary configuration of the flow restrictor 600 with a spherical or substantially spherical structure. As shown, the spherical structure is braided, but it may also be made by other processes (e.g. by laser cutting). The spherical structure can also be fabricated from the same piece of tubing (e.g, Nitinol tubing) with that of the device by laser cutting or chemical processes and then shape set to a larger diameter than the raw Nitinol tubing. The spherical structure can also be fabricated from the same piece of Nitinol tubing with that of the device by laser cutting or chemical processes and then shape set to a larger diameter than the raw Nitinol tubing.

In addition to removal device 111 of the invention, the proximal flow restrictor 600 can be combined and used with any existing clot retriever devices to restrict forward blood flow and help remove the clot from vasculature. For example, a proximal flow restrictor 600 of the invention may be used in combination with a morcellating device for removing emboli. In such instance, the proximal flow restrictor 600 is placed proximal to a blade used to morcellate the emboli.

As discussed above, radiopaque markers can be attached on any portion of the device for positioning (such as markers 116 and 118). Another way to gain visibility during use of the clot removal device 111 is to run a radiopaque material through the entire or partial lumen of the clot removal device 111.

The device 111 can have surface treatment on one or more of its various components (e.g. delivery member, transition member, expandable member, flow restrictor) to improve performance for those components of the device. For example, one or more components can either be coated or covered by typical biocompatible materials for lubricity entirely or partially. In addition, one or more components can have a positive or a negative charge for improved clot adhesion. Particularly, a surface of the expandable member 113 can have either a positive or negative charge for improved clot adhesion. In another example, the surface of one or more of the components can also be either mechanically or chemically treated to have a rough surface for improved clot adhesion. The rough surface can be achieved by, for example, 1) porous surface coating or layer; 2) micro-blasted surface or micro-pinning; 3) irregular strut geometry or arrangement.

FIGS. 11A and 11B illustrate a preferred embodiment of the expandable member 113 and flow restrictor 600. FIG. 11A illustrates the expandable member 113 in the compacted configuration. FIG. 11B illustrates the expandable member 113 in the expanded configuration. As shown in FIGS. 11A and 11B, the flow restrictor 600 is coupled to the proximal inner surface of the frame members 102 of the expandable member 113 such that the flow restrictor 600 expands along with expansion of the expandable member 113. The flow restrictor 600 is braided and forms a pouch-like in the inner lumen of the expandable member 113 to stop forward blood flow and create a vacuum to assist in clot removal. The frame members 104 of the expandable member 104 may include protrusions 340, valleys 330, or both to assist in clot removal. The protrusions 340 may be located at the intersection of two or more frame members 104 or along the length of a frame member 104. Generally, the protrusions are located on the peripheral of the frame. Likewise, the valleys 330 may be located at the intersection of the two or more frame members 104 or along the length of a frame member 104. In addition, the frame members 104 are intersecting to form openings 102 between the frame members 104. During use, the clot may enter the expandable member 113 through the openings 102, thereby integrating/engaging the clot with the expandable member 113 and reducing risk of clots breaking away or getting loose from the expandable member 113 during removal.

Figure 13A:
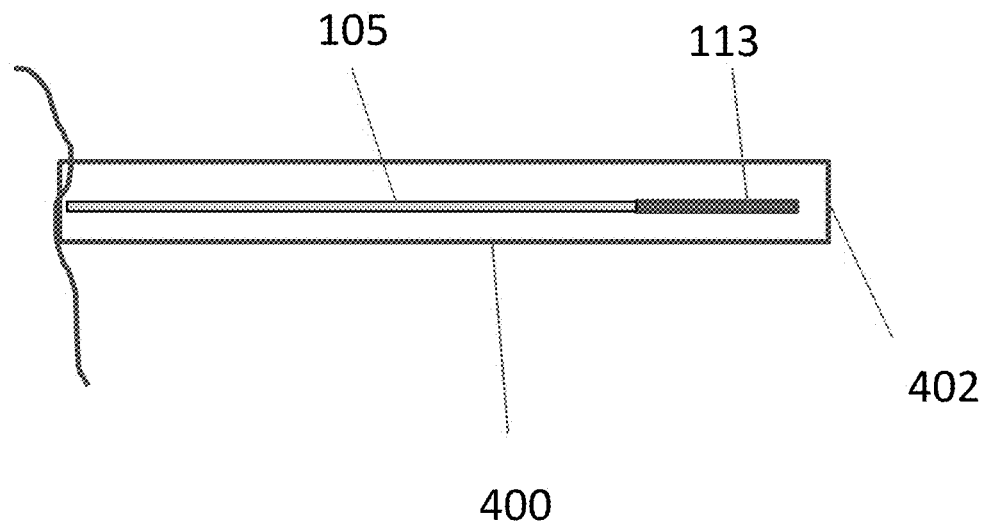
FIGS. 13A-13B illustrate deployment of the expandable treatment member from a delivery sheath.
Figure 13B:
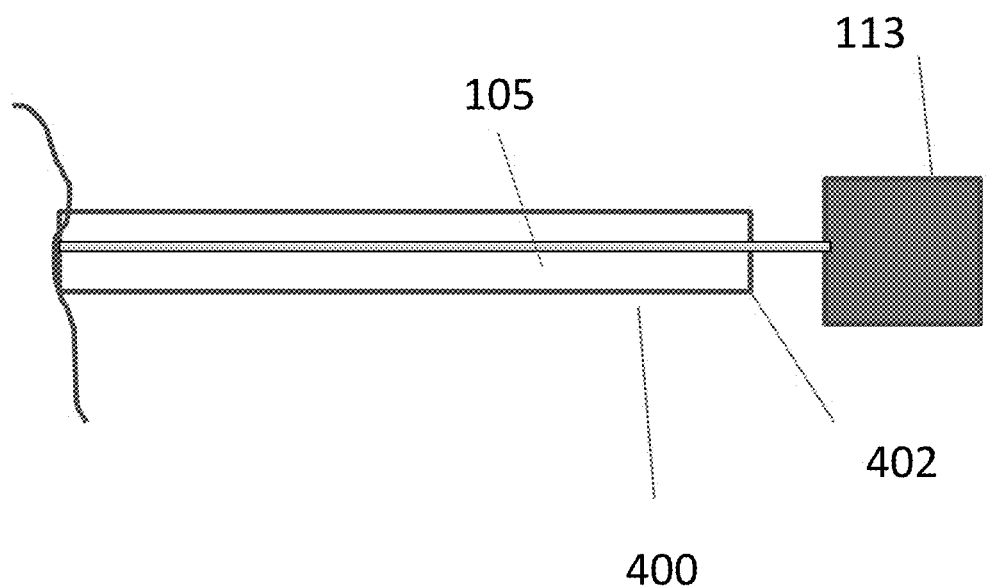

FIGS. 13A and 13B illustrate the expandable member 113 transitioning from the compacted configuration (FIG. 13A) to the expanded configuration (FIG. 13B), according to certain embodiments. The expandable member 113 may transition from the compacted configuration to the expanded configuration when the expandable member 113 is deployed from a delivery sheath 400. For example, a delivery sheath 400 may be positioned within a blood vessel, and a distal opening 402 of the delivery sheath may be positioned at or near, or distal to the blockage. The expandable member 113 is in the compacted configuration when disposed within a lumen of the delivery sheath 400. Once the delivery sheath 400 is placed as desired, the delivery member 105 can be used to push or deploy the expandable member 113 out of the opening 402 of the delivery sheath 400 and into the treatment area (e.g. into the blockage or distal to the blockage). In some embodiments, the expandable treatment member 113 is deployed by pushing the expandable treatment member 113 in the distal direction via the deliver member 105. In other embodiments, the expandable treatment member can be released/deployed from the delivery sheath 400, by withdrawing the sheath 400 proximately to expose the expandable treatment member 113. As the expandable member 113 is deployed, the expandable member 113 transitions from the compacted configuration to the expanded configuration, as shown in FIG. 13B.

In summary, the removal devices of the invention have several benefits over the prior art. The construction of the device from a single piece allows for a seamless transition from the delivery portion to the treatment portion, thus removing any joints or bonding of the two portions together as separate pieces. This improves the strength of the system as a whole and greatly reduces the possibility of the two parts unintentionally detaching from each other. Also, because the distal treatment portion is cut from a piece of material the same size as the proximal delivery portion, it allows the device to be compacted to a similar size profile giving it delivery advantages including a lower delivery force required and requiring small access systems. Additional delivery advantages from this design include the ability to manipulate the flexibility of the delivery system by varying the pitch size. In addition, a radiopaque marker can be attached within the lumen of the device to improve visualization. Lastly, the treatment portion's surface can be altered to enhance embolus affinity by either coating with a substance or changing the texture by mechanical or chemical means.

Compared with existing mechanical thrombectomy devices, the unique device design included in this invention has the advantage of 1) having proximal flow block/restriction feature to block the blood distal flow when the device is deployed during use; this feature can help to eliminate or reduce the risk of flush or break the clots during the procedure; 2) being made from a single piece of Nitinol super elastic material (such as tubing, etc.), Nitinol shape memory alloy material, or other biocompatible materials which exhibit super elastic or shape memory properties, thus giving the device a seamless transition from proximal delivery portion to distal therapeutic portion. This effectively removes any joints or bonding of a delivery wire with the treatment device, eliminating this physical weakness in the device and greatly reducing unintentional breakages during device delivery/retrieval. Another important advantage of the design disclosed in present invention is varies features (such as spiral cut, helix/coil configuration, etc.) can be implemented into device proximal delivery portion to achieve variable flexibility for easy delivery and navigation. The flexibility of the proximal delivery portion can vary from proximal to distal. For example, the distal portion can be more flexible than proximal portion. Furthermore, the device can achieve a smaller compacted profile, which reduces delivery and retrieval force and allows the physician to use smaller microcatheters for delivery to smaller vessels or the more distal vasculature. During the procedure, the flow restrictor can block the blood flow through the lumen of the device and the lumen of the treatment vessel segment, to help engage the clot and eliminate or reduce the risk to break the clot or flush the clots distal to the more distal vasculature.

INCORPORATION BY REFERENCE

References and citations to other documents, such as patents, patent applications, patent publications, journals, books, papers, and web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device for removing a blood clot in a vessel, the device comprising
    an elongate member configured for insertion into the vasculature, the elongate member comprising a distal end;
    an expandable member comprising a proximal portion that extends from the distal end of the elongate member, the expandable member configured to transition from a compacted state to an expanded state, in which the expandable member engages with the blood clot; and
    a flow restrictor configured to restrict blood flow and generate a low pressure zone at a location in the vasculature that is distal to the flow restrictor, the flow restrictor having a spherical structure that surrounds the proximal portion of the expandable member and the distal end of the elongate member, and having a neck portion that surrounds a length of the elongate member that extends proximal from the distal end of the elongate member.

2. The device of claim 1, wherein the elongate and expandable members are composed from a single piece of material.

3. The device of claim 2, wherein the single piece of material is Nitinol.

4. The device of claim 1, further comprising:
    an outer sheath defining a lumen and comprising a distal opening, wherein the elongate and expandable members are moveably disposed within the lumen of the outer sheath.

5. The device of claim 4, wherein the expandable member transitions into the expanded state when deployed from the distal opening of the outer sheath.

6. The device of claim 1, wherein the expandable member comprises a frame defining a plurality of openings.

7. The device of claim 6, wherein the frame further comprises a plurality of protrusions.

8. The device of claim 7, wherein the protrusions are located on the peripheral of the frame.

9. The device of claim 1, wherein the flow restrictor comprises a metal, a polymer, or a combination thereof.

10. The device of claim 1, wherein the flow restrictor comprises a material selected from group consisting of a netted material, a braided material, or a thin membrane.

11. The device of claim 1, wherein the flow restrictor covers a length extending between a proximal end of the expandable member to about ½ of the length of the expandable member.

12. The device of claim 1, wherein the flow restrictor covers a length extending between a proximal end of the expandable member to about ¼ of the length of the expandable member.

* * * * *